US007340292B2

(12) United States Patent
Li

(10) Patent No.: US 7,340,292 B2
(45) Date of Patent: Mar. 4, 2008

(54) BREAST CANCER DETECTION SYSTEM

(75) Inventor: Jian Li, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 209 days.

(21) Appl. No.: 10/778,973

(22) Filed: Feb. 13, 2004

(65) Prior Publication Data

US 2004/0167399 A1    Aug. 26, 2004

Related U.S. Application Data

(60) Provisional application No. 60/447,487, filed on Feb. 14, 2003.

(51) Int. Cl.
*A61B 5/05* (2006.01)

(52) U.S. Cl. ...................................... 600/430

(58) Field of Classification Search ................ 600/407, 600/430
See application file for complete search history.

(56) References Cited

U.S. PATENT DOCUMENTS

| 5,841,288 | A | * | 11/1998 | Meaney et al. | ............. 324/639 |
| 5,974,011 | A | | 10/1999 | Nakane | |
| 6,031,862 | A | | 2/2000 | Fullerton | |
| 6,061,589 | A | * | 5/2000 | Bridges et al. | ............. 600/430 |
| 6,104,942 | A | | 8/2000 | Kruger et al. | |
| 6,421,550 | B1 | | 7/2002 | Bridges et al. | |
| 6,448,788 | B1 | * | 9/2002 | Meaney et al. | ............. 324/637 |
| 6,567,688 | B1 | | 5/2003 | Wang | |
| 2003/0088180 | A1 | * | 5/2003 | Van Veen et al. | ........... 600/430 |
| 2005/0107693 | A1 | * | 5/2005 | Fear et al. | ................... 600/430 |

OTHER PUBLICATIONS

Surowiec et al., "Dielectric Properties of Breast Carcinoma and the Surrounding Tissues," IEEE Transactions on Biomedical Engineering, 35:257-263, 1988.
Fear et al., "Confocal microwave imaging for breast tumor detection: application to a hemispherical breast model," IEEE MTT-S Digest, 1759-1762, 2002.
Kruger et al., "Thermoacoustic Computed Tomography of the Breast at 434 MHz," IEEE MTT-S Digest, 591-594, 1999.
Kruger et al., "Thermoacoustic CT with Radio Waves: A Medical Imaging Paradigm," Thermoacoustics CT with Radio Waves, Radiology, 211:275-378, 1999.
Feng et al., "Microwave-induced thermoacoustic tomography: Reconstruction by synthetic aperture," Am. Assoc. Phys. Med., 28:2427-2431, 2001.

(Continued)

*Primary Examiner*—Brian L. Casler
*Assistant Examiner*—John F. Ramirez
(74) *Attorney, Agent, or Firm*—Akerman Senterfitt

(57) ABSTRACT

A method for detecting breast cancer can include the step of positioning a transmitting antenna and a receiving antenna about a breast so that the transmitting antenna is positioned to transmit microwave energy into the breast and the receiving antenna is positioned to receive the transmitted energy after the energy has passed into the breast. Microwave energy can be transmitted from the transmitting antenna. The microwave energy can be received by the receiving antenna and used to determine a presence of tumors within the breast. A relative position of the transmitting antenna and the receiving antenna can be adjusted about the breast. After each position adjustment, the transmitting and the receiving steps can be repeated.

13 Claims, 2 Drawing Sheets

OTHER PUBLICATIONS

Kruger et al., "Breast Cancer in Vivo: Constrast Enhancement with Thermoacoustic CT at 434 MHz-Feasibility Study," Radiology, 216:279-283, 2000.

Xu et al., "Exact Frequency-Domain Reconstruction for Thermoacoustic Tomography-II: Cylindrical Geometry," IEEE Transactions on Medical Imaging, 21:829-833, 2002.

Xu et al., "Exact Frequency-Domain Reconstruction for Thermoacoustic Tomography-I: Planar Geometry," IEEE Transactions on Medical Imaging, 21:823-828, 2002.

Xu et al., "Microwave-induced thermoacoustic tomography using multi-sector scanning," Am. Assoc. Phys. Med., 28:1958-1963, 2001.

Xu et al., "Time-Domain Reconstruction for Thermoacoustic Tomography in a Spherical Geometry," IEEE Transactions on Medical Imaging, 21:814-822, 2002.

Hagness et al., "Two-Dimensional FDTD Analysis of a Pulsed Microwave Confocal System for Breast Cancer Detection: Fixed-Focus and Antenna-Array Sensors," IEEE Transactions on Biomedical Engineering, 45:1470-1479, 1998.

Gabriel et al., "The dielectric properties of biological tissues: III. Parametric models for the dielectric spectrum of tissues," Phys. Med. Biol., 41:2271-2293, 1996.

Kruger et al., "Thermoacoustic CT," IEEE MTT-S Digest, WE3D-4:933-936, 2000.

Goscin et al., "Magnetic Resonance Imaging of the Breast," Cancer Control, 8:399-406, 2001.

Kinkel et al., "MR Imaging: breast Cancer Staging and Screening," Seminars in Surgical Oncology, 20:187-196, 2001.

Waxman, A., "PET:functional imaging applications in oncology," MEDICA/MUNDI, 46:12-18, 2002.

Kaul et al., "Early Dectection of Breast Cancer: Is Mammography Enough?," Hospital Physician, www.turner-white.com, 2002.

Gabriel et al., "The dielectric properties of Biological tissues: I. Literature survey," Phys. Med. Biol., 41:2231-2249, 1996.

Gabriel et al., "The dielectric properties of Biological tissues: II. Measurements in the frequency range 10Hz to 20GHz," Phys. Med. Biol., 41:2251-2269, 1996.

Li et al., "Efficient Super Resolution Time Delay Estimation Techniques," IEEE Conf. Acoustics, Speech, Signal Processing, May 12-15, 1998, pp. 2473-2476.

Meaney et al., "A Clinical Prototype for Active Microwave Imaging of the Breast", IEEE Trans. Microwave Theory & Tech., vol. 48, No. 11 (Nov. 2000).

Surowiec et al.., "Dielectric Properties of Breast Carcinoma & the Surrounding Tissues", IEEE Trans. Biomed Eng., vol. 35, No. 4, (Apr. 1988).

Chaudhary et al., "Dielectric Properties of Normal & Malignant Human Breast Tissue at Radiowave & Microwave Frequencies", IN J. of Biochem. & Biophy. vol. 21 pp. 76-79 Feb. 1984.

Joines et al. "Measured Electrical Prop. of Normal & Malignant Human Tissues from 50 to 900 MHz" Med. Phys. 21 (4), Apr. 1994.

Bulyshev et al. "Computational modeling of 3-dim. microwave tomography of breast cancer", IEEE Trans Biomed Eng. Sep. 2001; 48(9): 1053-6.

Semenov et al. "Microwave Tomography: 2-dim. System for Biological Imaging" IEEE Trans Biomed Eng. Sep. 1996; 43(9): 869-77.

Larsen et al. "Medical Applications of Microwave Imaging" IEEE Press, 1986.

Rius et al. "Planar & Cylindrical Active Microwave Temp. Imaging: Numerical Simulations", IEEE Trans on Med. Imag. vol. 11 No. 4, Dec. 1992.

Pakhomova et al. "Ultra-wide Band Electromagnetic Radiation Does Not Affect UV-induced Recombination & Mutagenesis in Yeast" Bioelectomagnetics vol. 19 No. 2 1998.

Lu et al. "Ultrawide-band Electrromagnetic Pulses Induced Hypotension in Rats" Physiol, Behav. 65 (4-5): 753-761, Jan. 1-15, 1999.

Wu et al. "Adaptive Ground Bounce Removal" Electronics Letters, vol. 37, No. 20, Sep. 27, 2001.

Li et al. "Efficient Mixed-Spectrum Estimation with Applications to Target Feature Extraction" IEEE Trans on Signal Proc., vol. 44, pp. 281-295, Feb. 1996.

Li et al. "An Efficient Algorithm for Time Delay Estimation" IEEE Trans on Signal Proc., vol. 46, No. 8, Aug. 1998.

Lebret "Antenna Array Pattern Synthesis via Convex Optimization" IEEE Trans. on Signal Proc., Vo. 45, pp. 526-532, Mar. 1997.

Li, et al. "Robust Autofocus Algorithm for ISAR Imaging of Moving Targets", IEEE Trans. on Aerospace Elect. Systems, vol. 31, pp. 613-627, Apr. 1996.

"Radio Waves Used to Screen for Breast Cancer, 2nd Phase of Testing to Begin in 6 Months" WNBC, posted Oct. 3, 2002.

Marchione "Detecting Changes in Breast Cancer Diagnosis: Mammograms more Accurate Biopsies Less Painful", JS Online, Oct. 10, 1999.

Burton, "Microwaves May Provide Early Detection of Breast Cancer", Newswise, Oct. 29, 1998.

Fear et al., "Enhancing Breast Tumor Detection with Near-Field Imaging," IEEE Microwave Magazine, 48-56, 2002.

National Academy of Sciences, "Excutive Summary," Mammography and Beyond: Developing Technologies for the Early Detection of Breast Cancer, http://www.nap.edu, 2003.

Newman, M., "Developing Technologies for Early Detection of Breast Cancer," A Public Workshop Summary, National Academy of Sciences, 2000.

National Acedemy of Sciences, "Executive Summary," A Review of the Department of Defense's Program for Breast Cancer Research, http://www.nap.edu, 2003.

Cady, B., "Breast Cancer in the Third Millennium," Journal of Surgical Oncology, 77:225-232, 2001.

Hagness et al., "Three-Dimensional FDTD Analysis of a Pulsed Microwave Confocal System for Breast Cancer Detection: Design of an Antenna-Array Element," IEEE Transactions on Antennas and Progapation, 47:763-791, 1999.

Kruger et al. "Thermoacoustic CT of the Breast," 4682-55, OptoSonics, Inc., http://www.optosonics.com, no date.

Wang et al., "Microwave-induced acoustic imaging of biological tissues," Rev. Sci. Instrum., 70:3744-3748, 1999.

Ku et al., "Combining Microwave and Ultrasound: Scanning Thermoacoustic Tomography," Proceedings of the 22nd Annual EMBS International Conference, Chicago, IL, 2321-2323, Jul. 23-28, 2000.

Chan et al., "Microwave-Induced Thermoelastic Tissue Imaging," Biomagnetic and Microwave Imaging, IEEE Engineering in Medicine & Biology Society 10th Annual International Conference, 1988.

Sun et al., "Time-frequency analysis for plastic landmine detetion via forward-looking ground penetrating radar," IEE Proc.-Radar Sonar Navig., 150:253-261, 2003.

Li et al., "Target Detection with Synthetic Aperture Radar," IEEE Transactions on Aerospace and Electronic Systems, 32:613-627, 1996.

Daniels, D., "An overview of RF sensors for mine detection: Part 3 Radar," http://demining.jrc.it/aris/events/mine99/Program/P41-47/MINE-RAD.htm, 1-9, Mar. 17, 2004.

De Jongh et al., "Design and analysis of new GPR antenna concepts," Delft University of Technology, Faculty of Information Technology and Systems International Research Centre for Telecommunications-transmission and Radar(IRCTR), no date.

Buchenauer et al., "Aperture Efficiencies of Impulse Radiating Antennas," Air Force Research Laboratory/DEHP, 91-108, 1999.

Stoica et al., "Robust Capon Beamforming," IEEE Signal Processing Letters, 10:172-175, 2003.

Yermakov, G., "The Exact Solution of the Problem of Ultra Wideband Signals Radiation by a Tem-Horn," DIPED-2002 Proceedings, 42-45.

Liu et al., "Pulse Radiation Antenna Feeded With a Face-to Face Tem Horn," IEEE, 447-450, 2000.

Li et al., "On Robust Capon Beamforming and Diagonal Loading," IEEE Transactions on Signal Processing, 51:1702-1715, 2003.

Li et al., "A Confocal Microwave Imaging Algorithm for Beast Cancer Detection," IEEE Microwave and Wireless Components Letters, 11:130-132, 2001.

\* cited by examiner

BREAST CANCER DETECTION SYSTEM

CROSS REFERENCE TO RELATED APPLICATIONS

This application claims the benefit of U.S. Provisional Application No. 60/447,487, filed in the United States Patent and Trademark Office on Feb. 14, 2003, the entirety of which is incorporated herein by reference.

BACKGROUND

1. Statement of the Technical Field

The present invention relates to the field of medical diagnostic imagery and, more particularly, to breast cancer detection systems.

2. Description of the Related Art

Breast cancer is the most common major cancer among women in the United States and breast cancer is the leading cause of cancer deaths in women, second only to lung cancer. An estimated 200,000 cases of breast cancer are diagnosed each year and more 43,300 lives are claimed in consequence. Significantly, in their lifetime, women of all ages have a one in eight chance of developing breast cancer. In consequence, early detection of breast cancer remains paramount to the survivability of victims of breast cancer. Though advances in the treatment of breast cancer have been made, the effectiveness of conventional breast cancer screening methods remains questionable.

Specifically, a decade-long study conducted amongst 260,000 Chinese women in Shanghai concluded that, in general, women examining their breasts remain unable to detect tumors early enough to reduce their risk of dying from breast cancer. To that end, Dr. Susan Love, a breast cancer surgeon, author of the text, "Dr. Susan Love's Breast Book", and president of the Susan Love Breast Cancer Foundation observed, "[B]y the time you can feel the cancer, it most likely has been present for about six to eight years. If it was going to spread, it has had ample opportunity."

The use of x-ray mammography for early breast cancer detection has not proven to be the silver bullet of breast cancer detection. In particular, the effectiveness of x-ray mammography has been questioned at all levels. Notably, recent studies show that while x-ray mammography screening in older women can reduce the probability of dying of breast cancer by thirty percent, the reduction is much less for younger women. In this regard, much of problem with x-ray mammography relates to the inability for x-ray mammography to image dense tissue.

Consequently, the results of an x-ray mammography may show suspicious areas where no malignancy exists (up to twenty percent of biopsied growths identified as cancerous by a mammogram are identified as malignancies). Furthermore, radiologists interpreting x-ray mammography imagery can overlook between fifteen and twenty-five percent of cancers. Finally, the current process for conducting x-ray mammography can be severely uncomfortable. Specifically, the use of imaging plates can cause bruising in the breasts and can, therefore, be a significant disincentive for women to undergo mammography screening.

Notably, in the past five years, microwave imagery has formed the basis of a new, alternative detection technique useful in the early detection of breast cancer. Conventional X-ray mammography utilizes high-energy ionizing radiation that is passed through the breast to a photographic plate in order to shadow potential tumors. In contrast, microwave detection utilizes an array of antennae affixed to the breast surface that can "bounce" non-ionizing microwave radiation off malignant growths whose radiation can be detected by the array. Based upon the characteristics of the "bounce" growths can be detected much in the same way that radar can be used to detect objects at a distance.

Not surprisingly, microwave imaging for use in breast cancer detection has been referred to as "breast tumor radar". In a typical implementation, a computer can be coupled to an array of small antennae beaming 6 GHz pulsed microwaves. As normal breast tissue remains largely transparent to microwave radiation, breast tumors contain more water causing the scattering of the beamed microwaves back toward their source. The antennae can detect the scattered microwaves which can be analyzed to construct a three-dimensional image showing both the location and size of the tumor.

Microwave imaging based upon the water content of the tumor has been used in the applications of both ultrawideband radar technology and confocal optical microscopy. Such applications can exploit the dielectric contrast between normal breast tissue and malignant tumors at microwave frequencies. Specifically, each element in an antenna array can sequentially illuminate an uncompressed breast with a low-power ultrawideband microwave pulse. Following the acquisition of backscattered waveforms, the array can be synthetically focused by time shifting and adding the recorded returns. A subsequent synthetic scan of the focal point permits the detection of strong scattering sites in the breast, which can be identified as malignant tumors.

Nevertheless, confocal microwave imaging techniques for breast cancer detection remain unable to precisely differentiate malignancies from benign tumors, largely due to the imprecise modeling of the breast. More particularly, conventional confocal microwave imaging systems for breast cancer detection rely upon either a planar or cylindrical modeling of the breast. For the planar configuration, the patient can be oriented in a supine position with the breast being modeled as a flat plane having infinite dimensions. By comparison, for the cylindrical configuration, the patient can be oriented in a prone position with breast being modeled as an infinitely long cylinder. Yet, in reality, the shape and size of any given breast can vary from person to person. Moreover, irregularities can persist about the boundary between the breast skin and surrounding tissue and also about the boundary between the breast tissue and the chest wall.

SUMMARY OF THE INVENTION

The present invention relates to the field of microwave imaging system for breast cancer detection. Using one embodiment of the present invention, the deficiencies of conventional confocal microwave imaging can be overcome in that neither a cylindrical nor a planar modeling configuration for breasts is necessary. Rather, in accordance with the inventive arrangements, the microwave imaging system can produce accurate detection of small to large tumors in the breast with specific reference to the shape, size, and boundary irregularities of the breast under study. Importantly, so as to avoid the inaccuracies of the planar and cylindrical configurations, variably positioned probing antennae can be affixed to the breast surface. The actual position of the probing antennae can be determined through the use of a fixed position array of passive antennae. In this way, the breast can be modeled in accordance with the actual size and shape of the breast under study, and unnecessary generic models can be avoided, thereby increasing the accuracy of tumor detection over conventional methodologies.

It is presumed that irregularities exist at the boundary between breast surface and breast tissue, and again at the boundary between breast tissue and chest cavity. Accordingly to one embodiment of the invention, the effect of microwave scattering caused by each boundary can be sensed, computed, and removed from the composite signal response produced by a microwave scan of the breast. As a result, cancerous tumors, even at early stages where the cancerous tumors are small in size, can be detected notwithstanding the relative weakness of a signal reflection produced by the early stage cancerous tumor.

Additionally, in accordance with the subject matter disclosed herein, sidelobe levels can be reduced so that weak objects can be seen clearly without becoming masked by the sidelobes of strong objects. Specifically, a sidelobe control process can be selected from the group consisting of optimal shading and spectral estimation. In optimal shading, a convex optimization process can be applied to properly shade detected objects. By comparison, in a spectral estimation process, mixed spectrum estimation techniques can be applied to the detected microwave signal to perform target feature extraction. In both cases, tumors of significantly small size (and hence early stage) can be detected.

One particular aspect of the present invention includes a method for detecting breast cancer. The method can include the step of positioning a transmitting antenna and a receiving antenna about a breast so that the transmitting antenna is positioned to transmit microwave energy into the breast and the receiving antenna is positioned to receive the transmitted energy after the energy has passed into the breast. Microwave energy can be transmitted from the transmitting antenna. For example, an ultrawideband microwave transmission can be conveyed by the transmitting antenna utilizing a stepped frequency transmission technique. The microwave energy can be received by the receiving antenna and used to determine a presence of tumors within the breast. A relative position of the transmitting antenna and the receiving antenna can be adjusted about the breast. After each position adjustment, the transmitting and the receiving steps can be repeated. The transmitting and receiving steps can be performed multiple times to generate a composite scan of the breast.

In one embodiment, clutter attributable to a boundary between breast tissue and adjacent tissue can be reduced using a time delay estimation technique, such as a relaxation based algorithm. In another embodiment, an image of the breast can be displayed using microwave imaging based upon the composite scan. Further, optimal shading can be applied to the image to reduce undesirable sidelobe effects. A spectral estimation technique can also be applied to the image.

In a particular embodiment, a position of the transmitting antenna and/or the receiving antenna can be determined using a passive array of antenna. The passive array of antenna can determine the position of the two antennas based upon energy either transmitted by or perturbed by one or more of the antennas.

Another aspect of the present invention can include a system for detecting breast cancer. The system can include a microwave transmitting antenna, a receiving antenna, and a signal processor. The transmitting antenna and the receiving antenna can be positioned about a breast and can be adjusted relative to one another. The signal processor can determine a presence of a tumor within the breast based upon computations involving microwave energy transmitted by the transmitting antenna, microwave energy received by the receiving antenna, and the relative positions of the transmitting antenna and the receiving antenna. In one embodiment, the transmitting antenna and the receiving antenna can be independently positionable about the breast. In another embodiment, the system can include an antenna array that can determine a position of the transmitting antenna and/or the receiving antenna. In such an embodiment, the antenna array is not physically linked to the transmitting antenna. The system can also include a microwave imaging system configured to display an interior image of the breast based upon microwave energy detected by the receiving antenna.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE INVENTION

The present invention provides a microwave imaging process and system for use in breast cancer detection. The process can include the steps of transmitting microwave energy from a first probing antenna at the surface of the breast inwardly through the breast tissue, receiving at a second probing antenna at the surface of the breast reflected ones of the transmitted microwave energy which had been reflected by a tumor disposed in the breast tissue, and further receiving in an array of fixed position antennae emissions from said transmitted microwave energy. The position of the probing antennae can be computed based upon position location techniques applied to the time of receipt of the emissions. Based upon computed position, an image of the tumor in the breast tissue can be formed.

Importantly, clutter reduction can be applied to the formation of the image of the tumor so as to reduce the effect of microwave energy reflected not by the tumor, but by the boundaries between breast skin and breast tissue, and breast tissue and chest wall. In that regard, a weighted Fourier transform and relaxation based algorithm, such as a Lagrangian relaxation algorithm, can be applied to reflected signal to reduce the clutter. Additionally, the formation of the image can be enhanced by applying a modified periodogram technique for parameter estimation to the reflected signal so as to reduce sidelobe levels of the reflected signal. In this way, the microwave imaging process of the present invention can detect very small tumors which ordinarily could not be detected by conventional confocal microwave imagery.

Figure 1:
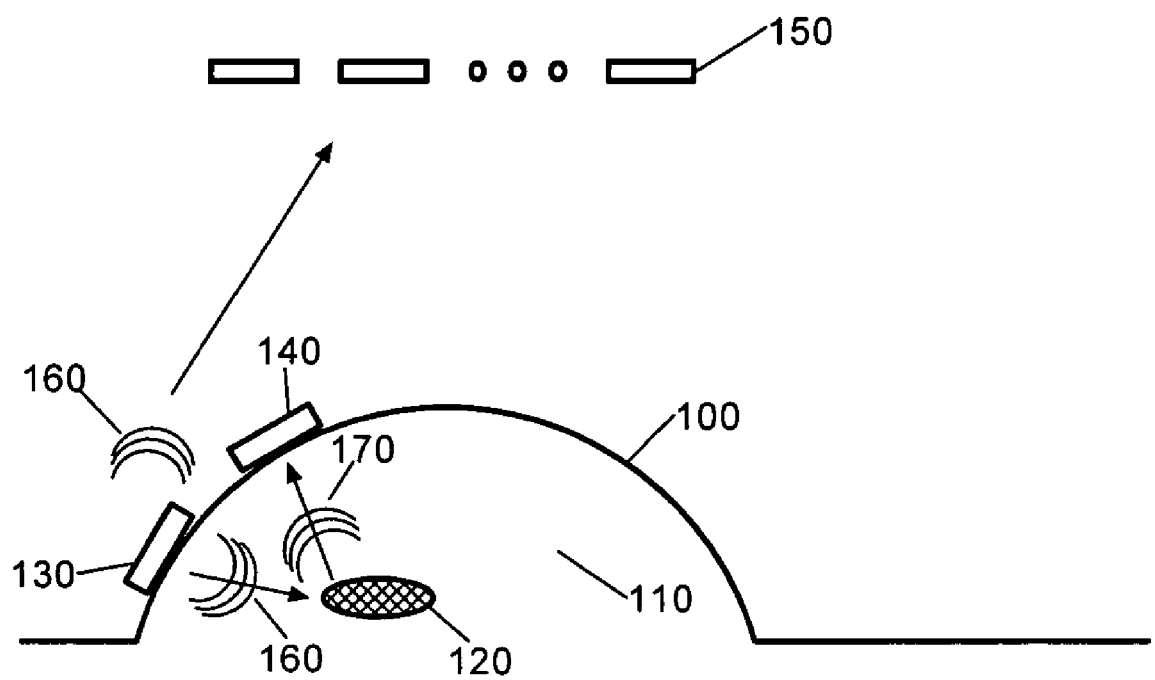
FIG. 1 is a schematic illustration of a microwave imaging system configured for breast cancer detection using both probing antennae and a passive antennae array; and, FIG. 2 is a schematic illustration of the microwave imaging system of FIG. 1 configured to detect and eliminate signal portions attributable to the breast skin/breast tissue boundary, and to the breast tissue/chest wall boundary.

FIG. 1 is a schematic illustration of a microwave imaging system configured for breast cancer detection using both probing antennae and a passive antennae array. As shown in FIG. 1, at least one transmitting antenna 130 can be coupled to the breast 100 under study. Additionally, at least one receiving antenna 140 also can be coupled to the breast 100. The transmitting antenna 130 can transmit ultrawideband microwave radiation 160 towards the breast tissue 110 in which a tumor 120 can be disposed. The transmission of the radiation 160 can be either of the stepped frequency transmission type, or the impulse radar type, though it will be recognized by the skilled artisan that stepped frequency radar is easier to control in terms of transmitted signals and easier to manipulate in terms of received signals.

If a tumor 120 is present within the breast tissue 110, the tumor 120 will reflect the ultrawideband microwave radiation 160 to produce scattered (phase shifted) radiation 170. The receiving antenna 140 can detect the scattered radiation 170 and a delay between the transmission and receipt of the radiation 160, 170 can be computed. Significantly, the computation of the delay can suffice merely to determine the range from the antennae 130, 140 and the tumor 120. Locating the incident surface of the tumor 120 within the breast tissue 110, however, requires knowledge of the position of the antennae 130, 140. To that end, the passive array of antennae 150 can detect the transmitted radiation 160. Differential times of arrival for the transmitted radiation 160 at each element of the array of antennae 150 can be recorded, based upon which the position of the antennae 130, 140 can be computed.

In this way, the antennae 130, 140 can be moved about the surface of the breast 100 and the forgoing process can be repeated so as to form a composite scan of the breast. It will be recognized by one skilled in the art that by permitting the free movement and positioning of the antennae 130, 140 about the breast 100, breasts of all shapes and sizes can be accommodated while not limiting the data reduction of the imaging analysis to a single, generic breast of either planar or cylindrical configuration. Accordingly, the configuration illustrated within FIG. 1 demonstrates a marked advantage over the conventional confocal microwave imaging techniques of the prior art.

It will be recognized by the skilled artisan, that signal enhancement and exploitation are critical for early breast cancer detection using microwave imaging. Although the contrast in dielectric properties between normal and cancerous breast tissue can be quite significant in the microwave frequency range, early cancer detection still can be challenging. Accordingly, to further enhance the ability of the microwave imaging system of the present invention to identify otherwise small tumors in breast tissue, clutter and sidelobe reduction techniques can be applied to the breast cancer detection system shown in FIG. 1.

Figure 2:
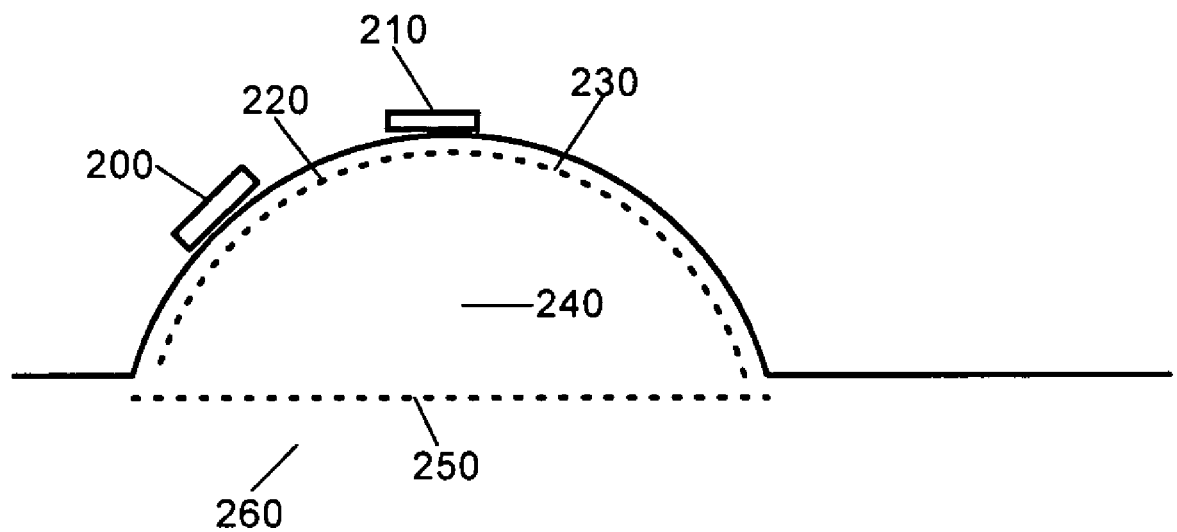

In further illustration, FIG. 2 is a schematic illustration of the microwave imaging system of FIG. 1 configured to detect and eliminate signal portions attributable to the breast skin/breast tissue boundary, and to the breast tissue/chest wall boundary. Since cancerous tumors in the breast tissue 240 can be small in size at the earliest stages of breast cancer, any microwave signal transmitted by the transmitting antenna 200 and reflected by early stage tumors can be weak and difficult to detect in the receiving antenna 210. To complicate matters, reflections from the boundary 230 between breast skin 220 and breast tissue 240, and the boundary 250 between breast tissue 240 and the chest wall 260 can create "clutter" which must be discounted so as not to obscure reflected energy from cancerous tumors.

To reduce unwanted clutter from the imaging analysis, the signal response attributable to the boundary 230 between breast skin 220 and breast tissue 240 can be removed in the same manner that ground bounce can be removed from the detection of landmines using ultrawideband radar. Specifically, the responsiveness of the boundary 230 and 250 can be determined according to the well known problem of super resolution time delay estimation. Once such time delay estimation technique can include known weighted Fourier transformation and relaxation based (WRELAX) algorithms.

When applying confocal microwave imaging to the problem of breast cancer detection, individual received datum can be aligned for all positions of the probing antennae 200, 210 based upon detected delays between transmission of the energy and arrival of the reflected energy. Once aligned to a focal point, the data can be summed to produce an image. Yet, the delay and sum approach can produce significant undesirable effects, such as unusually large sidelobes. Notably, the problem can be compounded where the antenna sensors have not been properly aligned.

To counteract the sidelobe effect, optimal shading can be determined based upon convex optimization techniques known in the art. When applying optimal shading to aligned data, an image of a tumor can be discerned from the sidelobes of strongly reflecting objects. By comparison, in the absence of optimal shading, the image of a tumor can be obscured by the sidelobes of strongly reflecting objects. In any case, as a second option, spectral estimation can be applied to the reconstruction of an image. To that end, in a preferred aspect of the present invention, an iterative beam removing algorithm such as the CLEAN algorithm can be applied to the signal to reduce the effect of large sidelobes of strongly reflecting objects.

Finally, it will be recognized by the skilled artisan inaccuracies produced by errors in detecting the precise position of the probing antennae 200, 210 can have a blurring effect on a resulting confocal image. Consequently, in a preferred aspect of the present invention, auto-focusing techniques can be applied to the signal to reduce blurring. Specifically, an AUTOCLEAN algorithm can be applied to the produced imagery so as to remediate blurring effects caused by errors in the position location of the probing antennae 200, 210.

The AUTOCLEAN algorithm is a parametric algorithm based upon a flexible data model which takes into account arbitrary range migration and arbitrary phase errors across the synthetic aperture that may be induced by unwanted radial motion of the target as well as propagation or system instability. Known in the art, AUTOCLEAN can be classified as a multiple scatterer algorithm (MSA), but it differs considerably from other existing MSAs in several aspects. It will be further recognized that AUTOCLEAN is computationally efficient and involves only a sequence of fast Fourier transforms.

Notably, the methodology of the present invention can be realized in hardware, software, or a combination of hardware and software. An implementation of the heuristic routing method of the present invention can be realized in a centralized fashion in one computer system, or in a distributed fashion where different elements are spread across several interconnected computer systems. Any kind of computer system, or other apparatus adapted for carrying out the methods described herein, is suited to perform the functions described herein.

A typical combination of hardware and software could be a general purpose computer system with a computer program that, when being loaded and executed, controls the computer system such that it carries out the methods described herein. The present invention can also be embedded in a computer program product, which comprises all the features enabling the implementation of the methods described herein, and which, when loaded in a computer system is able to carry out these methods.

Computer program or application in the present context means any expression, in any language, code or notation, of a set of instructions intended to cause a system having an information processing capability to perform a particular function either directly or after either or both of the following a) conversion to another language, code or notation; b) reproduction in a different material form. Significantly, this invention can be embodied in other specific forms without departing from the spirit or essential attributes thereof, and accordingly, reference should be had to the following claims, rather than to the foregoing specification, as indicating the scope of the invention.

What is claimed is:

1. A method for detecting breast cancer comprising the steps of:
   coupling a plurality of transmitting antennas to surface portions of a breast and transmitting microwave energy from each of said transmitting antennas, each of the transmitting antennas being moveable to accommodate a shape and size of said breast;
   coupling a plurality of receiving antennas to different surface portions of the breast and receiving reflected microwave energy via each of said receiving antennas, each of the receiving antennas being moveable to accommodate a shape and size of said breast;
   positioning a passive array of antennas at a location remote from said transmitting and receiving antennas to detect the transmitted microwave energy;
   recording arrival times corresponding to when each antenna of the passive array of antennas detects the transmitted microwave energy and computing based upon the recorded arrival times a corresponding differential arrival time of the transmitted microwave energy at each antenna of the passive array;
   computing relative positions of the plurality of transmitting antennas and the plurality of receiving antennas based upon differential arrival times;
   adjusting a relative position of at least one of said transmitting antennas and said receiving antennas on said breast; and
   repeating said transmitting and said receiving steps after adjusting said relative position, wherein the received microwave energy is used to determine a presence of tumors within said breast.

2. The method of claim 1, wherein said transmitted step transmits ultrawideband microwave energy using a stepped frequency transmission technique.

3. The method of claim 1, performing said adjusting and said repeating steps a plurality of times to generate a composite scan of said breast.

4. The method of claim 1, further comprising the steps of:
   displaying an image of said breast using microwave imaging based upon said received microwave energy; and
   applying an auto-focusing technique to mitigate blurring of said image.

5. The method of claim 1, further comprising the steps of:
   displaying an image of said breast using microwave imaging based upon said received microwave energy; and
   applying a spectral estimation technique to said image.

6. The method of claim 1, further comprising the step of:
   reducing clutter attributable to a boundary between breast tissue and adjacent tissue using a time delay estimation technique, wherein said time delay estimation technique utilizes a weighted Fourier transformation and Lagrangian relaxation algorithm.

7. A system for detecting breast cancer comprising:
   a plurality of microwave transmitting antennas configured to be attached to respective surface portions of a breast to transmit microwave energy into said breast, each of the transmitting antennas being moveable to accommodate a shape and size of said breast;
   a plurality of receiving antennas configured to be attached to respective surface portions of said breast to receive microwave energy reflected from said breast, each of the receiving antennas being moveable to accommodate a shape and size of said breast;
   a passive array of antennas positioned at a location remote from said transmitting and receiving antennas to detect the transmitted microwave energy;
   a processor to compute a differential arrival time of the transmitted microwave energy at each antenna of the passive array based upon recorded arrival times corresponding to when each antenna of the passive array of antennas detects the transmitted microwave energy, and to compute relative positions of the plurality of transmitting antennas and the plurality of receiving antennas based upon the differential arrival times;
   a signal processor configured to determine a presence of a tumor within said breast based upon computations involving microwave energy transmitted by said transmitting antenna, microwave energy received by said receiving antenna, and the relative positions of said transmitting antenna and said receiving antenna.

8. The system of claim 7, wherein said transmitting antenna and said receiving antenna are independently positionable on said breast.

9. The system of claim 7, further comprising:
   a microwave imaging system configured to display an interior image of said breast based upon microwave energy detected by the receiving antenna.

10. A system for detecting breast cancer comprising:
    a plurality of transmitting antennas configured to be attached to respective surface portions of a breast to transmit microwave energy into the breast, each of the transmitting antennas being moveable to accommodate a shape and size of said breast;
    a plurality of receiving antennas configured to be attached to different respective surface portions of the breast to receive microwave energy reflected from the breast, each of the receiving antennas being moveable to accommodate a shape and size of said breast;
    a passive array of antennas positioned at a location remote from said transmitting and receiving antennas to detect the transmitted microwave energy;
    a means for determining differential arrival times of the transmitted microwave energy at each antenna of the passive array based upon when each antenna of the passive array of antennas detects transmitted microwave energy and for positioning said transmitting antennas and said receiving antennas on said breast so that said transmitting antennas are positioned to transmit microwave energy into said breast and said receiving antennas are positioned to receive said transmitted energy after said energy has passed into said breast, the positioning of said transmitting and receiving antennas being based upon the determined differential arrival times;
    a means for adjusting a relative position of said transmitting antenna and said receiving antenna on said breast to generate a composite scan of said breast;

a means for determining a presence of tumors within said breast that utilizes repeated microwave transmissions, said transmissions occurring with said transmitting antenna and said receiving antenna located in different positions relative to each other about said breast.

11. The system of claim 10, further comprising:

a microwave imaging system configured to display an interior image of said breast based upon the detected microwave energy; and means for applying an auto-focusing technique to mitigate blurring of said image.

12. The system of claim 10, wherein said means for displaying is further configured to include means for enhancing said image using a spectral estimation technique.

13. The system of claim 10, further comprising:

means for reducing clutter attributable to a boundary between breast tissue and adjacent tissue using a time delay estimation technique based upon, wherein said time delay estimation technique utilizes a weighted Fourier transformation and Lagrangian relaxation algorithm.

* * * * *